(12) United States Patent
Kim et al.

(10) Patent No.: US 7,705,589 B2
(45) Date of Patent: Apr. 27, 2010

(54) SENSOR FOR DETECTING SURFACE DEFECTS OF METAL TUBE USING EDDY CURRENT METHOD

(75) Inventors: Young Joo Kim, Daejeon (KR); Bong Young Ahn, Daejeon (KR); Seung Seok Lee, Daejeon (KR); Young Gil Kim, Daejeon (KR); Dong Jin Yoon, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 144 days.

(21) Appl. No.: 12/033,059

(22) Filed: Feb. 19, 2008

(65) Prior Publication Data

US 2009/0206830 A1  Aug. 20, 2009

(51) Int. Cl.
*G01N 27/82* (2006.01)
(52) U.S. Cl. ........................................ 324/240; 324/228
(58) Field of Classification Search ......... 324/219–221, 324/228, 237–238, 240–243, 262
See application file for complete search history.

(56) References Cited

U.S. PATENT DOCUMENTS

| 4,084,136 | A | * | 4/1978 | Libby et al. | 324/238 |
| 4,673,877 | A | * | 6/1987 | Sakamoto et al. | 324/225 |
| 4,683,361 | A | * | 7/1987 | Driggers | 219/644 |
| 5,068,608 | A | * | 11/1991 | Clark, Jr. | 324/220 |
| 5,438,262 | A | * | 8/1995 | Nanjyo et al. | 324/238 |
| 7,528,599 | B2 | * | 5/2009 | Zimmerman | 324/242 |

* cited by examiner

*Primary Examiner*—Bot L LeDynh
(74) *Attorney, Agent, or Firm*—Whitham Curtis Christofferson & Cook, PC (57) ABSTRACT

A sensor for detecting surface defects of a metal tube solves a problem of a conventional eddy current probe in that it is difficult to detect a crack in the circumferential direction of a metal tube. The sensor includes a plurality of coils wound at a predetermined inclined angle. The plurality of coils is inserted into the inside of a metal tube. Alternating current is applied to the coils to measure a change in impedance of the coils due to a change in an eddy current generated in the metal tube, thus detecting a surface defect of the metal tube.

10 Claims, 11 Drawing Sheets

SENSOR FOR DETECTING SURFACE DEFECTS OF METAL TUBE USING EDDY CURRENT METHOD

BACKGOUND OF THE INVENTION

1. Field of the Invention

The present invention relates to a sensor for detecting surface defects of a metal tube using an eddy current method. More particularly, the present invention relates to a sensor for detecting surface defects of a metal tube, which can solve a problem of a conventional eddy current probe in that it is difficult to detect a crack in the circumferential direction of a metal tube.

2. Description of Related Art

When a conductor is placed close to a coil through which an alternating current flows, a magnetic field generated around the coil acts on the conductor. Since the magnetic field of the coil is generated by the alternating current, the direction of magnetic flux which penetrates the conductor is continuously changed with time.

Here, an electromotive force, which acts to oppose the change in the magnetic flux penetrating the conductor, is generated in the conductor. Such a phenomenon is called electromagnetic induction, and the electric current induced in the conductor by the electromotive force is called an eddy current.

When a discontinuity is present in the conductor (test object), the magnitude and distribution of the eddy current are changed, and a method of detecting the discontinuity in the conductor using the above phenomenon is directed to an eddy current testing.

Accordingly, the eddy current testing is available only when the test object is a conductor.

The magnitude and distribution of the eddy current induced in the conductor are changed by the frequency, the electrical conductivity and permeability of the conductor, the size and shape of the test object, and the defect such as a crack. Accordingly, with the detection of the change in the eddy current flowing in the test object, it is possible to detect whether or not a defect is present in the test object and evaluate the quality of material.

However, the alternating current or the eddy current flowing in the conductor has a property called a skin effect, in which the current concentrates on the surface of the conductor, and thus the alternating current or the eddy current is significantly reduced as coming close to the inside of the conductor. The degree of the reduction is significantly increased if the frequency, and the electrical conductivity and permeability of the conductor are high.

Accordingly, the eddy current testing is more useful in detecting a defect on the surface or in the vicinity of the surface than a defect inside the test object.

The eddy current testing is a surface defect detection method, mainly used in the manufacture of tubes, wires and rods and in the repair inspection of them.

For example, the eddy current testing can be used in the repair inspection of heat exchanger tubes, aircraft parts, and the like, to which other testing methods are hard to apply.

The eddy current testing is widely used for various purposes such as the measurement of electrical conductivity of nonferrous alloys including copper, copper alloy and aluminum alloy, the measurement of film thickness of plating material, and the like, in addition to the purpose of the defect detection.

The quality inspection by the eddy current testing can effectively detect foreign materials in the test object in a mass production line.

The basic principle of the eddy current testing will be described with reference to FIG. 15 below.

The eddy current is a swirling current induced in a conductor by a magnetic flux (an alternating current magnetic field in general) changed with time. When an electric current flows in a conducting wire, a magnetic field is generated around the conducting wire. In this case, if the conducting wire is a coil and the electric current is an alternating current, the phase of the alternating current is changed with time, and thus a magnetic flux changed with time can be obtained.

When the coil is brought close to a test object (conductor), an eddy current is generated in the test object. The eddy current generated in the test object creates another magnetic field in the opposite direction, thus causing a change in impedance of the test coil.

At this time, if there is a defect in the test object, the change in the impedance of the test coil differs, and thus it is possible to detect the defect in the test object by measuring the change in the impedance. Moreover, since the impedance is also varied by a change in properties of the material such as electrical conductivity and permeability, it is possible to identify the properties of the material by measuring the change.

Figure 15:
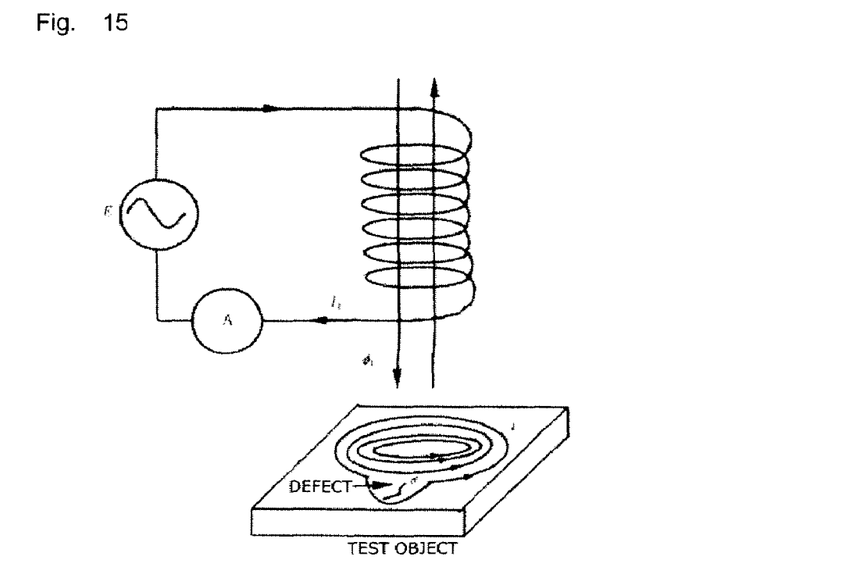
FIG. 15 is a conceptual diagram illustrating a basic principle of an eddy current testing.

In more detail, as shown in FIG. 15, when an alternating current $I_1$ flows in a test coil, a first magnetic field $\phi_1$ is generated around the test coil. An eddy current i is induced in a test object by the thus generated first magnetic field $\phi_1$, and the eddy current creates a second magnetic field $\phi_2$ in a direction opposite to the magnetic field $\phi_1$.

As a result, the electric current $I_1$ is changed into $I_2$. At this time, if a defect such as a crack is present in the test object, the value of the second magnetic field is changed, and thus the value of the electric current $I_2$ is also changed.

Accordingly, the measurement of the changed value enables the eddy current testing to be available.

Meanwhile, in an eddy current testing apparatus for detecting defects based on the above-described principle, the test coil may be classified according to its detection method into a single coil method and a double coil method.

The single coil method (or self inductance) is directed to a method using a single coil.

In accordance with the single coil method, the coil induces the eddy current in the test object by an alternating current power source, and a change in the generated eddy current is detected at the same time. Moreover, since the change in the eddy current generated due to a defect present in the test object is detected with the change in the impedance, the coil is connected to a bridge circuit. Since this method performs the generation and detection of the eddy current in the signal coil, the production is easy, and it is widely used due to a high detection efficiency.

Figure 12:
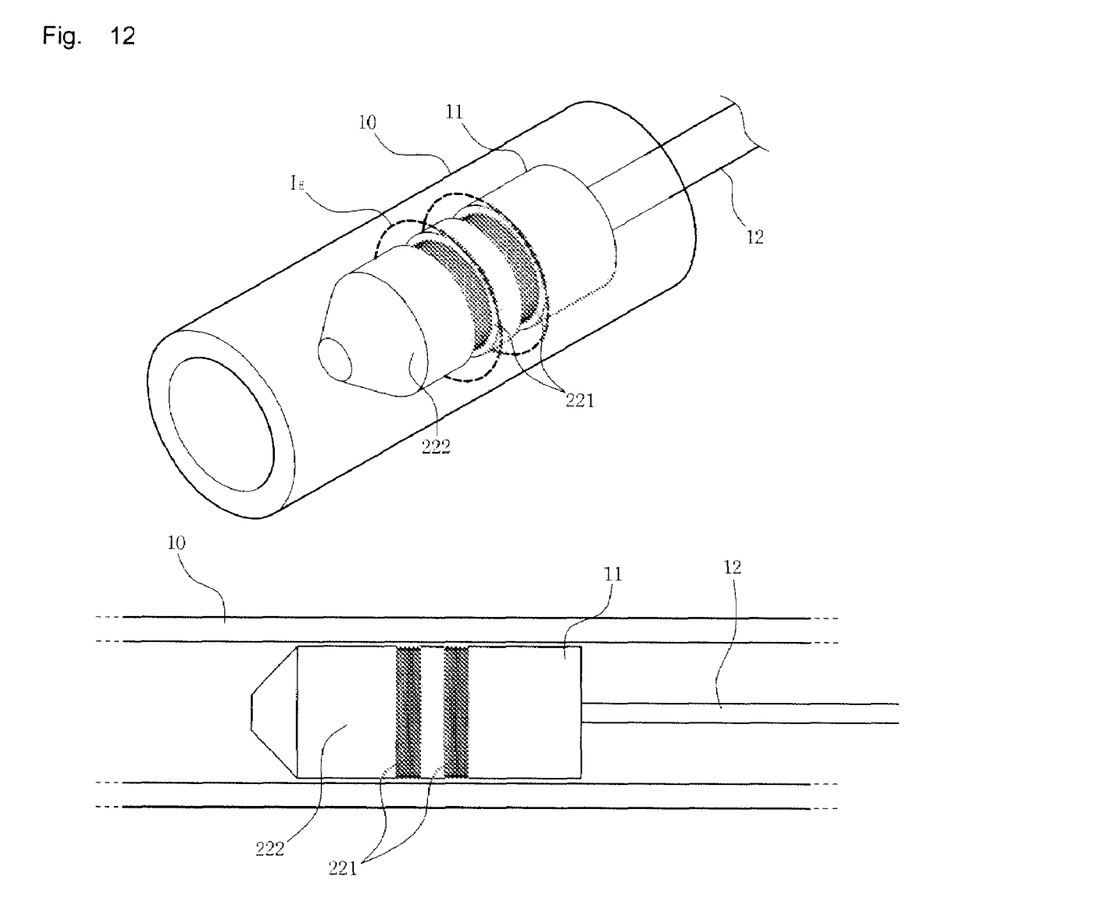

The double coil method (or mutual inductance) uses two coils as shown in FIG. 12. That is, the two coils include a first coil for inducing a magnetic field by an alternating current power source to generate an eddy current and a second coil for detecting a change in the eddy current. Accordingly, the first coil is called an exciting coil 222 and the second coil is called a receiving coil 221 or a pick-up coil.

The test coil may be classified according to its test method into an absolute method and a differential method. These methods are classified according to the way the coil is electrically connected.

The absolute method is directed to a method which uses a single coil to detect all changes in a region where the test coil is located without comparison with the same test object to be tested or with a comparative sample.

The differential method is directed to a method which uses more than two coils to compare changes in two regions where the test coils are located.

Moreover, the differential method may be classified according to the object to be compared into a self comparison and a mutual comparison.

The self comparison compares two regions of the same sample with each other by arranging two coils in the two regions to be tested.

Figure 11:
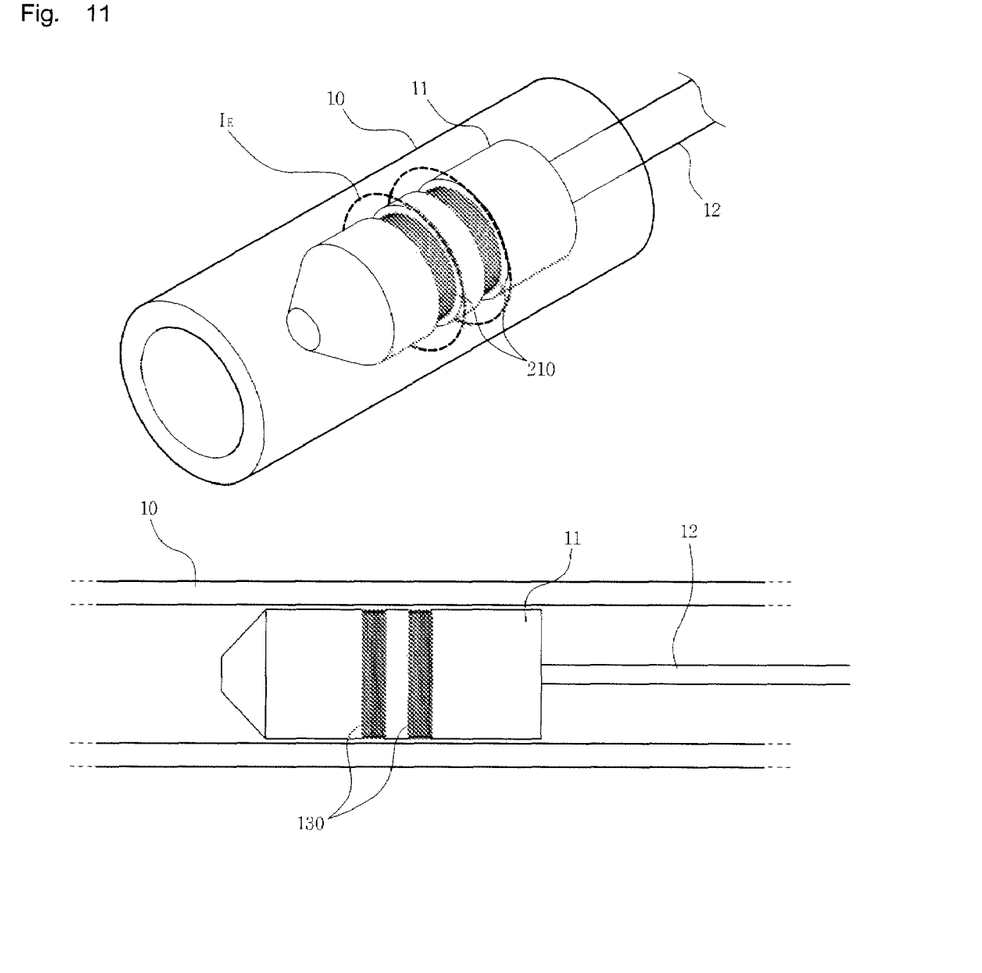
FIGS. 11 to 14 are schematic diagrams showing conventional eddy current probes.

Referring to FIG. 11, two regions in the same test object are compared with each other. Here, if there is no difference in the two regions where two test coils 210 are located, an output signal is not generated.

However, if a defect is present in any one of two regions, a change is detected and thus an output signal is generated. Accordingly, the self comparison coils 210 show a drastic change for the defect such as a crack, not for the detection such as a minute difference of electrical conductivity, a change in shape, and the like. Accordingly, the self comparison method is widely used as the test coils for the defect detection and, more particularly, much used in the automatic detection.

However, the self comparison has a drawback in that, if two coils are positioned in two defects having the same magnitude in the test object, it is considered that there is no change, and thus the testing is impossible.

Moreover, the application method of the coil is changed according to the shape of the test object.

Figure 13:
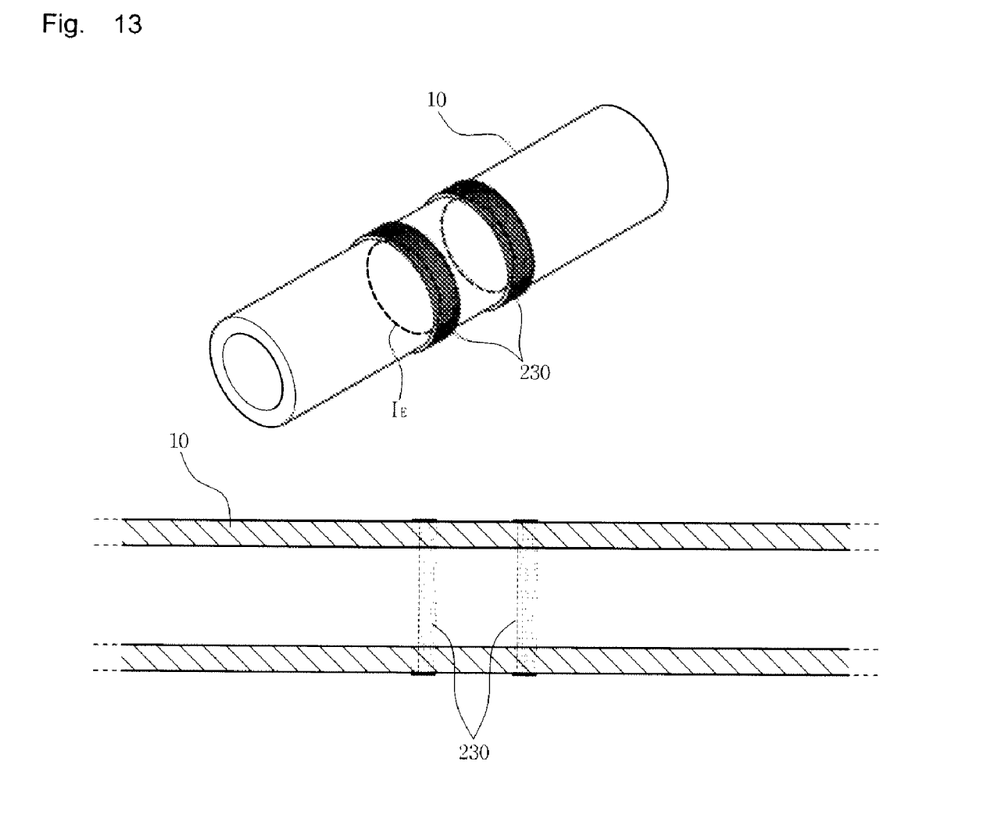
Figure 14:
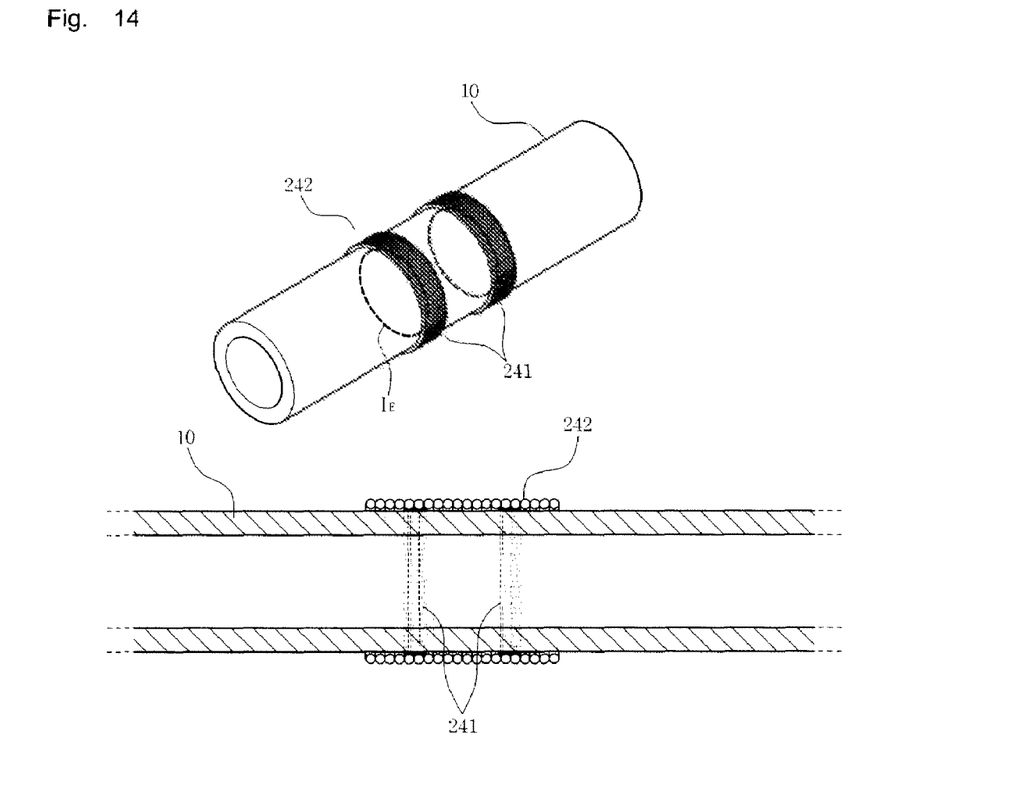

As shown in FIGS. 13 and 14, an encircling coil is directed to a testing method in which a test object passes through the inside of coils 230 and 241 to perform the test Accordingly, the encircling coil is suitable for the inspection of rods, wires and tubes. Moreover, the encircling coil shows a high sensitivity in detecting a defect in an axial direction vertical to an eddy current generated in the longitudinal direction in a tubular or rod-like test object.

Moreover, since the encircling coil is positioned outside the test object, it is more suitable for the surface defect detection than the inside defect detection. Here, it is important to consider a filling factor so that the coil is closely adjacent to the outside of the test object and to prevent eccentricity from occurring between the test object and the coil during the test.

Meanwhile, as shown in FIGS. 11 and 12, an inside coil is directed to a testing method in which coils 210 and 221 penetrate the inside of a tubular test object to perform the test, and also called a bobbin coil and an inner coil. The inside coil is mainly applied to the inspection of an inner diameter of a tube and a bolt hole. Moreover, the inside coil shows a high sensitivity in detecting a defect in the axial direction like the encircling coil and is more suitable for the inside defect detection than the surface defect detection.

Here, the change in the eddy current by the defect is affected by the size, direction and depth of the defect and, in the case where the defect is vertical to the direction that the eddy current flows, the largest signal is generated.

The reason for this is, as described with respect to the basic principle of the eddy current testing, that the eddy current induced in the conductor generates the second magnetic field in the opposite direction to the first magnetic field of the test coil to induce a change in the impedance of the test coil. As a result, when a defect is formed in a direction vertical to the eddy current flow direction, the discontinuity which obstructs the eddy current flow is increased to induce the largest change in the impedance of the test coil.

However, in case of the conventional test coil (probe), since the coil is wound in the circumferential direction, the direction of a magnetic force line (magnetic field) is an axial direction of a metal tube, and the eddy current flow direction by the magnetic force line is a circumferential direction the same as that the coil is wound.

Accordingly, the conventional probe is useful in detecting the defect generated in the axial direction; however, it is not effective in detecting the defect generated in the circumferential direction.

The information disclosed in this Background of the invention section is only for enhancement of understanding of the background of the invention and should not be taken as an acknowledgement of any form of suggestion that this information forms the prior art that is already known to a person skilled in the art.

SUMMARY OF THE INVENTION

The present invention is directed to a sensor for detecting surface defects of a metal tube, in which a coil for an eddy current testing is wound at a predetermined inclined angle, not in the circumferential direction, thus detecting all defects generated in the circumferential direction as well as the axial direction.

In one aspect, the present invention provides a sensor for detecting surface defects of a metal tube, the sensor comprising a plurality of coils wound at a predetermined inclined angle, wherein the plurality of coils is inserted into the inside of a metal tube and an alternating current is applied to the coils to measure a change in impedance of the coils due to a change in an eddy current generated in the metal tube, thus detecting a surface defect of the metal tube.

The plurality of coils may perform the roles of an exciting coil for generating an eddy current and a sensing coil for detecting the change in the impedance of the coils at the same time so as to detect a defect using a principle that a balance of a voltage induced in one coil and a voltage induced in the other coil is broken when the defect passes through one of the coils.

The plurality of coils may be divided into an exciting coil for generating an eddy current and a sensing coil provided on the outside of the exciting coil and detecting the change in the impedance of the coils, the sensing coil detecting a change in the eddy current generated in the metal tube by applying an alternating current to the exciting coil.

Each of the plurality of coils may have a different inclined angle.

The plurality of coils may have a different inclined angle and wound symmetrical with respect to a virtual line vertical to an axial direction.

The plurality of coils may have the same inclined angle and wound parallel to each other.

In another aspect, the present invention provides a sensor for detecting surface defects of a metal tube, the sensor comprising a plurality of coils wound at a predetermined inclined angle, wherein the plurality of coils is inserted into the outside of a metal tube and an alternating current is applied to the coils to measure a change in impedance of the coils due to a change in an eddy current generated in the metal tube, thus detecting a surface defect of the metal tube.

The plurality of coils may perform the roles of an exciting coil for generating an eddy current and a sensing coil for detecting the change in the impedance of the coils at the same time so as to detect a defect using a principle that a balance of a voltage induced in one coil and a voltage induced in the other coil is broken when the defect passes through one of the coils.

The plurality of coils may be divided into an exciting coil for generating an eddy current and a sensing coil provided on the outside of the exciting coil and detecting the change in the impedance of the coils, the sensing coil detecting a change in the eddy current generated in the metal tube by applying an alternating current to the exciting coil.

Each of the plurality of coils may have a different inclined angle.

The plurality of coils may have a different inclined angle and wound symmetrical with respect to a virtual line vertical to an axial direction.

The plurality of coils may have the same inclined angle and wound parallel to each other.

BRIEF DESCRIPTION OF THE DRAWINGS

The above and other features of the present invention will be described with reference to certain exemplary embodiments thereof illustrated the attached drawings in which.

DETAILED DESCRIPTION OF THE INVENTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

FIGS. 1 to 10 are diagram illustrating a sensor for detecting surface defects of a metal tube in accordance with preferred embodiments of the present invention.

An eddy current generated in a test object creates another magnetic field in the opposite direction to induce a change in impedance of a test coil. At this time, if there is a defect in the test object (metal tube 10), the change in the impedance of the test coil differs, and thus it is possible to detect the defect in the test object by measuring the change in the impedance.

As described above, the eddy current testing performs an inspection by detecting the change in the impedance of the coil, and the factors affecting the sensitivity of the inspection can be identified by examining the factors affecting the impedance of the coil.

Among them, the important factors include electrical conductivity, discontinuity, permeability and distance between the test object and the coil. The discontinuity is highly affected by a defect which is present in the vicinity of the surface.

Meanwhile, when a defect such as a crack is formed in a direction vertical to the direction (circumferential direction) that the eddy current flows, the change in the impedance of coils 110 and 120 due to the defect is maximized.

However, since the conventional winding methods of coils 210, 221, 222, 230, 241 and 242 wind the coils in the direction vertical to the axial direction in the event that the test object has a tubular shape, the direction of an eddy current $I_E$ is the circumferential direction, and it is advantageous for the detection of a defect in the axial direction; however, it has a limitation in that it cannot detect a defect in the circumferential direction.

In order to solve the above-described drawback, the present invention winds a coil at a predetermined inclined angle with respect to the axial direction, and thus it is possible to detect a defect formed in the circumferential direction, differently from the conventional method in which the coil is wound in a direction vertical to the axial direction.

The preferred embodiments of the present invention provide the following four types of coil winding methods.

(1) Inside Bridge Type

Figure 1:
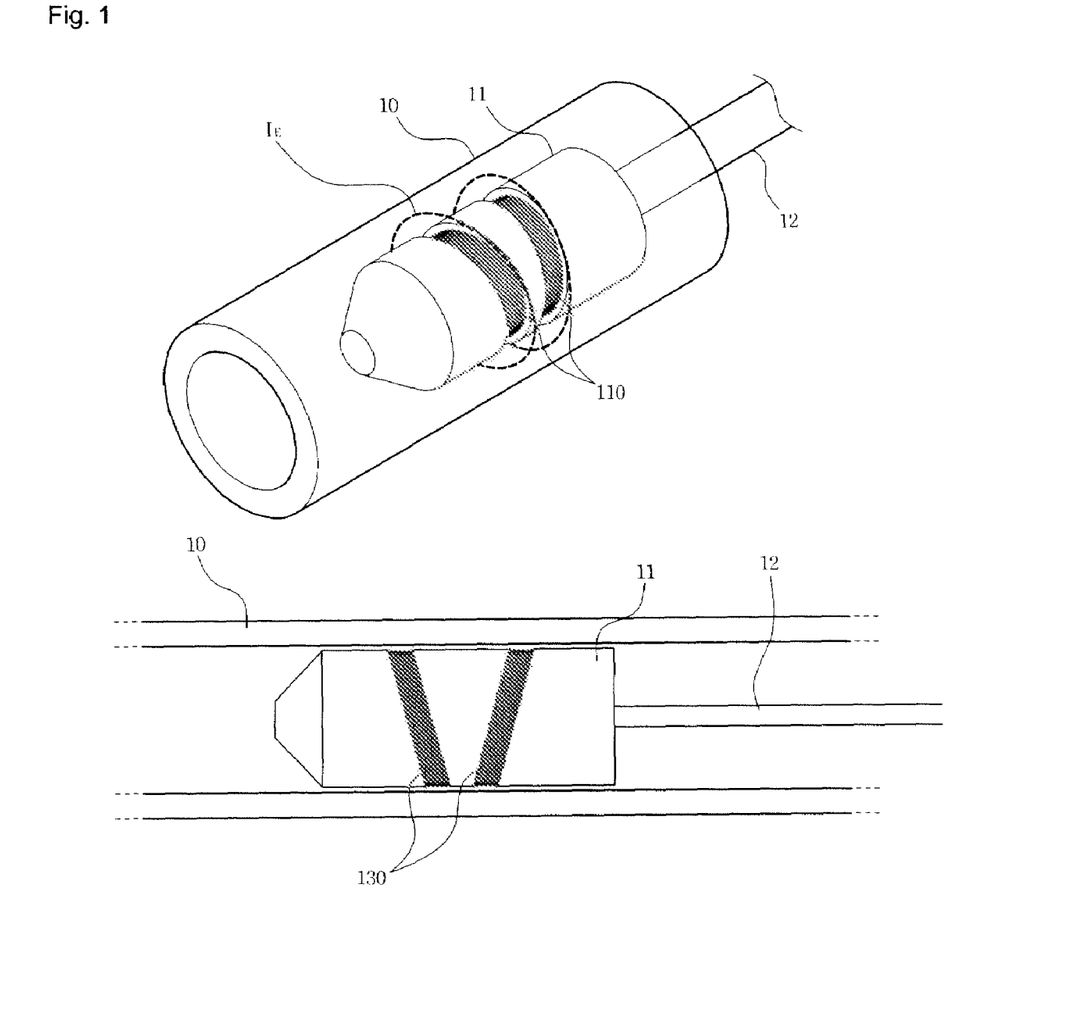
FIGS. 1 and 2 are perspective views showing an inside bridge type probe in accordance with a preferred embodiment of the present invention.
Figure 2:
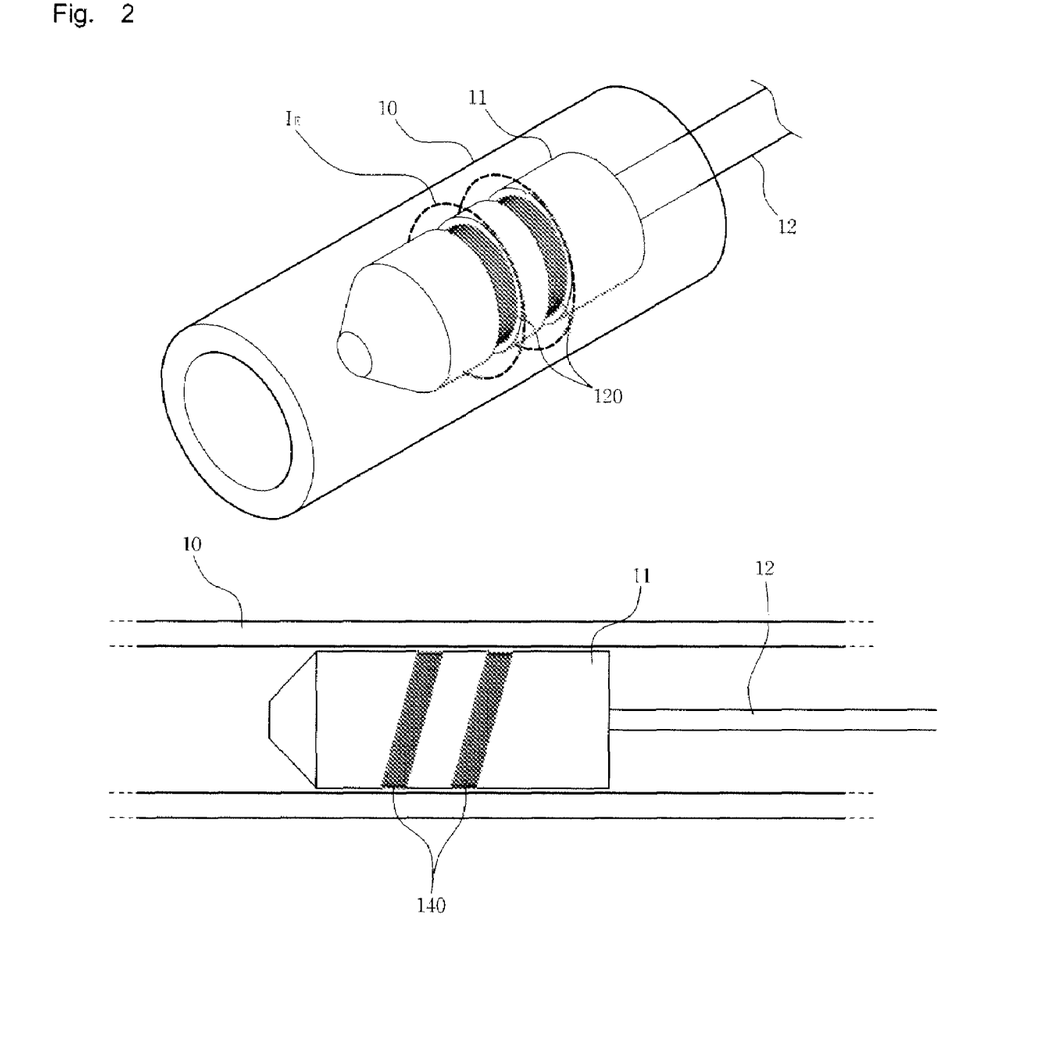

FIGS. 1 and 2 are perspective views showing an inside bridge type probe in accordance with a preferred embodiment of the present invention.

The inside bridge type probe has a structure in which a coil support 11 having winding grooves is inserted into the inside of a metal tube 10 and two coils 110 are wound on the coil support 11 symmetrically to each other at a predetermined inclined angle. In this case, the two coils 110 perform the roles of an exciting coil for generating an eddy current $I_E$ and a sensing coil for detecting a change in the impedance at the same time, and a central axis 12 is provided on one side of the coil support 11.

Moreover, the inside bridge type probe may have a structure in which the coil support 11 having the winding grooves is inserted into the inside of the metal tube 10 and two coils 120 are wound on the coil support 11 parallel to each other at a predetermined inclined angle.

(2) Inside Send-receive Type

Figure 3:
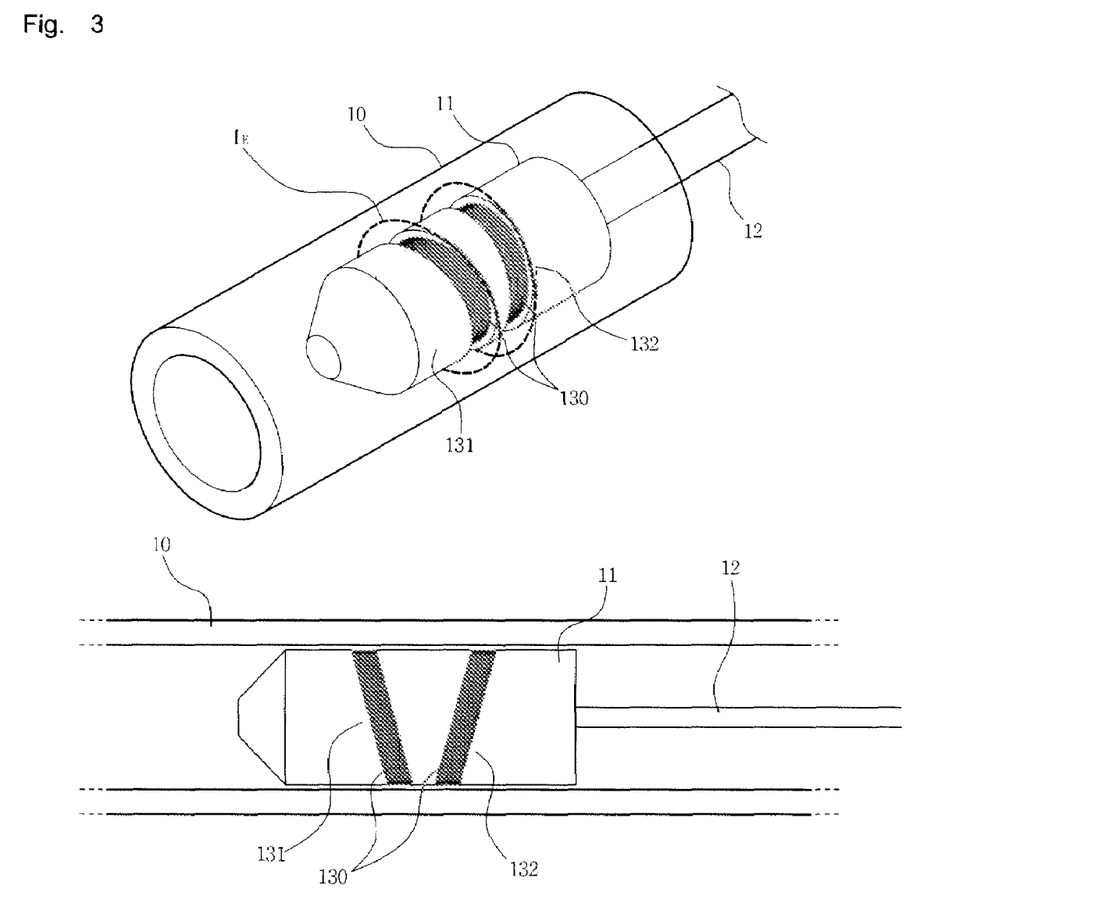
FIGS. 3 and 4 are perspective views showing an inside send-receive type probe in accordance with another preferred embodiment of the present invention.
Figure 4:
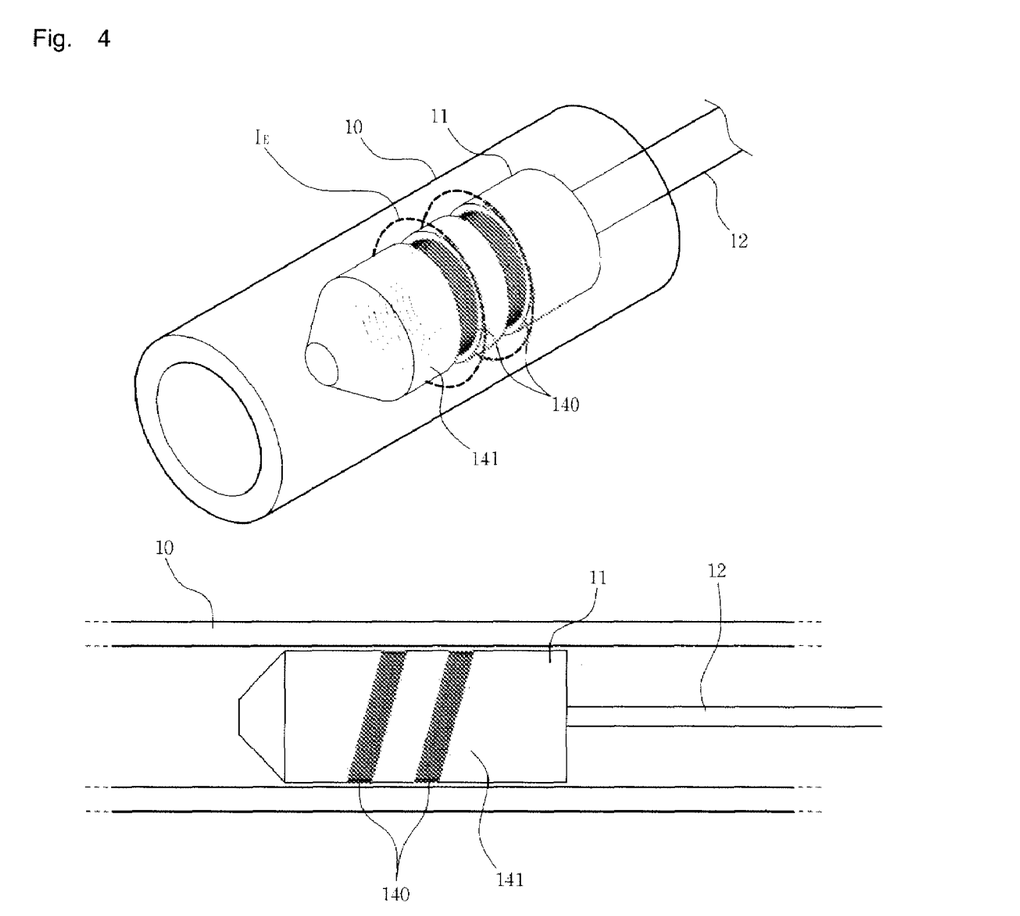

FIGS. 3 and 4 are perspective views showing an inside send-receive type probe in accordance with another preferred embodiment of the present invention.

The inside bridge type probe has a structure in which a coil support 11 having winding grooves is inserted into the inside of a metal tube 10 and two coils 130 and 131 are wound on the coil support 11 symmetrically to each other at a predetermined inclined angle. In this case, unlike the inside bridge type probe, the inside send-receive type probe has a structure in which an exciting coil 131 for generating an eddy current $I_E$ and a sensing coil 130 for detecting a change in the impedance are separately provided and the exciting coil 131 is provided in the inside of the sensing coil 130.

Moreover, the inside send-receive type probe may have a structure in which the coil support 11 having the winding grooves is inserted into the inside of the metal tube 10 and two coils 140 are wound on the coil support 11 parallel to each other at a predetermined inclined angle.

(3) Encircling Bridge Type

Figure 5:
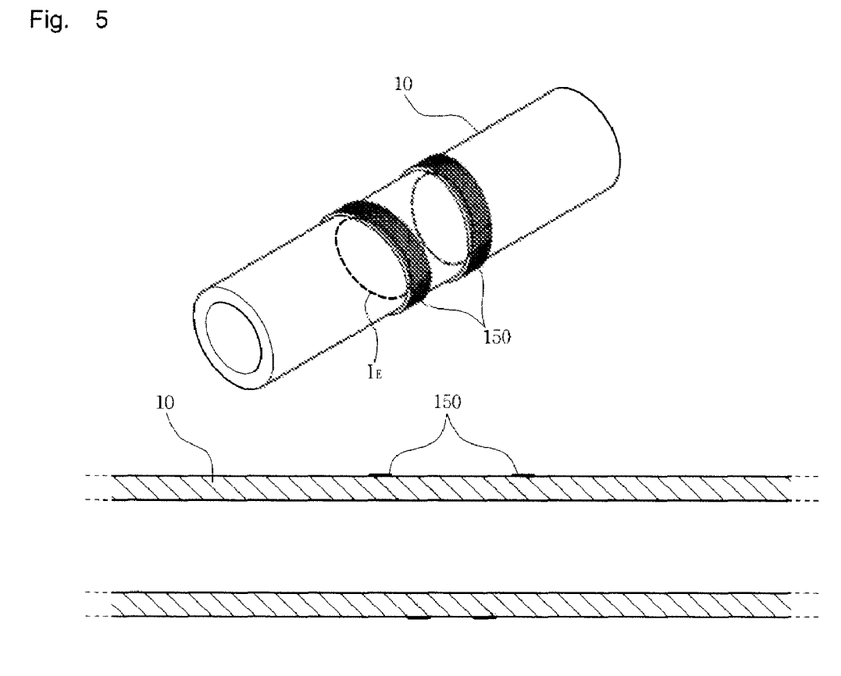
FIGS. 5 and 6 are perspective views showing an encircling bridge type probe in accordance with still another preferred embodiment of the present invention.
Figure 6:
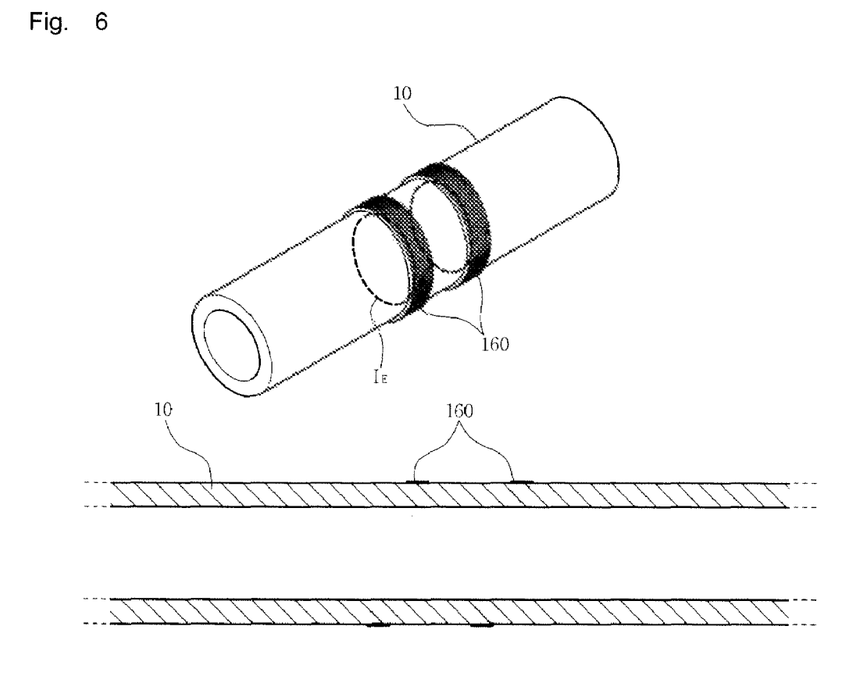

FIGS. 5 and 6 are perspective views showing an encircling bridge type probe in accordance with still another preferred embodiment of the present invention.

The encircling bridge type probe has a structure in which the outside of a metal tube 10 is encircled with two coils 150 arranged symmetrically to each other at a predetermined angle. In this case, the two coils 150 perform the roles of an exciting coil for generating an eddy current $I_E$ and a sensing coil for detecting a change in the impedance at the same time.

Moreover, the encircling bridge type probe may have a structure in which the outside of a metal tube 10 is encircled with two coils 160 and the two coils 160 are wound parallel to each other at a predetermined angle.

(4) Encircling Send-receive Type

Figure 7:
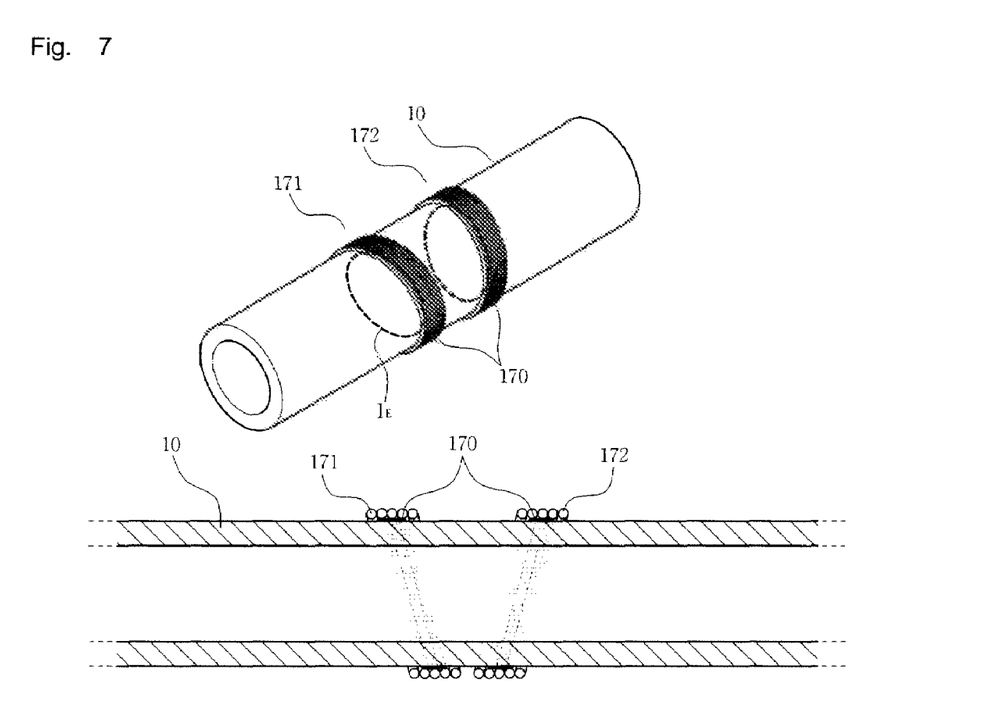
FIGS. 7 and 8 are perspective views showing an encircling send-bridge type probe in accordance with yet another preferred embodiment of the present invention.
Figure 8:
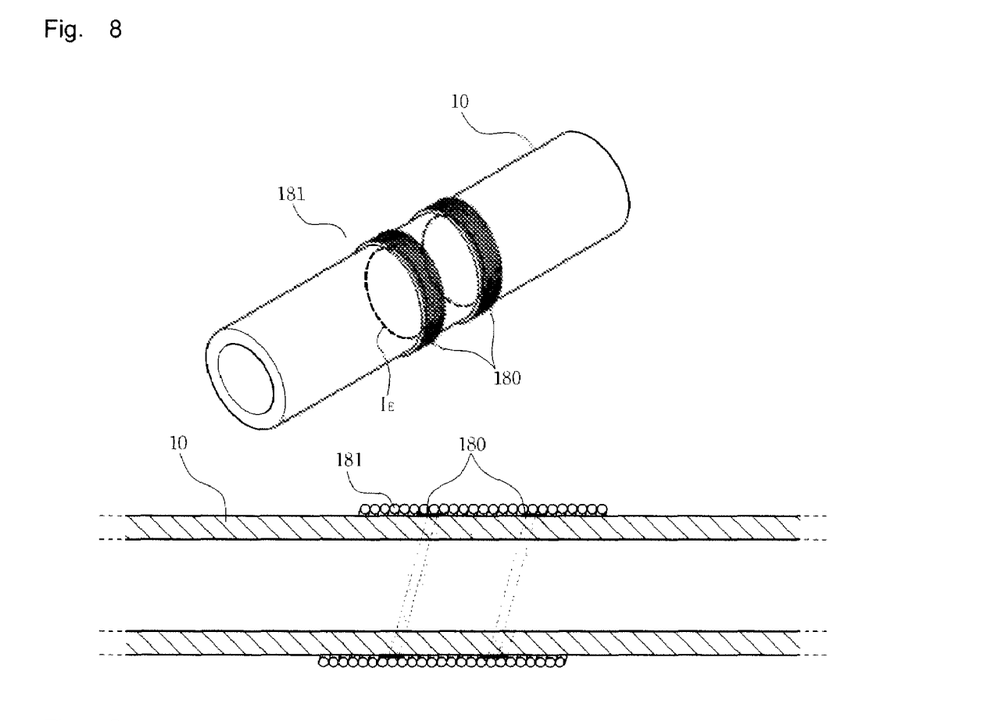

FIGS. 7 and 8 are perspective views showing an encircling send-receive type probe in accordance with yet another preferred embodiment of the present invention.

The encircling send-receive type probe has a structure in which the outside of a metal tube 10 is encircled with two coils 170 and 171 arranged symmetrically to each other at a predetermined angle. In this case, unlike the encircling bridge type probe, the encircling send-receive type probe has a structure in which an exciting coil 171 for generating an eddy current $I_E$ and a sensing coil 170 for detecting a change in the impedance are separately provided and the exciting coil 171 is provided in the outside of the sensing coil 170.

Moreover, the encircling send-receive type probe may have a structure in which the outside of a metal tube 10 is encircled with two coils 180 and the two coils 180 are wound parallel to each other at a predetermined angle.

Figure 9:
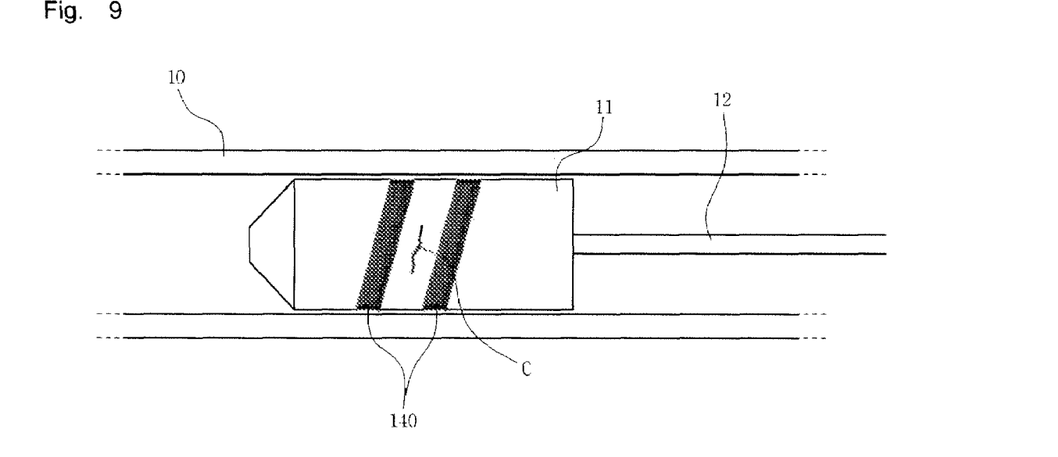
FIGS. 9 and 10 are diagrams illustrating a defect detection method in a case where a defect of a metal tube is parallel to a winding direction of any one of two coils in FIGS. 3 and 4.
Figure 10:
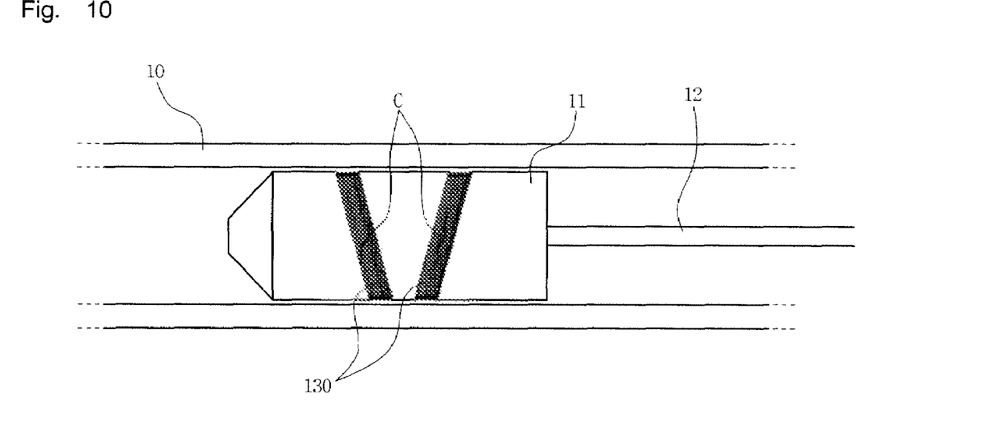

FIGS. 9 and 10 are diagrams illustrating a defect detection method in a case where a defect of a metal tube is parallel to a winding direction of any one of two coils in FIGS. 3 and 4.

Among the above-described four coil winding methods, the method in which the coils 140 are provided parallel to each other at the same inclined angle has a drawback in that it is difficult to detect a defect C generated parallel to the winding direction of the coils 140 on the surface of the metal tube 10.

Accordingly, in order to effectively detect the defect C, it is preferable that the coils 130 are wounded on the coil support 11 symmetrically to each other at a predetermined inclined angle, and thus it is possible to detect a defect which is not detected by the coils 140 wound at the same inclined angle. In this case, the center line of the symmetry is a line vertical to the axial direction.

Especially, in order to solve the problem that the winding method of the coils 140 arranged at the same inclined angle has, the two coils may be arranged at different inclined angles; however, when one coil is wound at an inclined angle and the other coil is wound in the vertical direction thereto, the defect detection efficiency is increased.

The operation state of the sensor for detecting surface defects of the metal tube 10 having the above-described configuration in accordance with the present invention will be described below.

Although the above embodiments have been described with reference to four types of coil winding methods, the basic operation of the present invention is substantially the same.

When an alternating current is applied to the coils 110, 120, 150 and 160 (exciting coils 131, 141, 171 and 181 in case of the send-receive type), an alternating current magnetic field is generated around the coils by the applied current. When the alternating current magnetic field is applied to the metal tube 10, a voltage is induced in the inside of the metal tube 10 in accordance with Faraday's law, and a current flows around the surface of the metal tube by the thus induced voltage, which is called the eddy current $I_E$. The intensity and phase of the eddy current $I_E$ differs according to the quality of the metal and whether or not there is a defect.

The eddy current $I_E$ creates a second magnetic field, and the magnetic field interferes with the original magnetic field to cause a change in magnitude and phase of the voltage induced in the coil. The bridge type probe (including a coil support 11 and coils) uses two coils to compare the magnitudes of the voltages induced in the respective coils. That is, the bridge type probe detects a defect using a principle that the balance of the voltages induced in the two coils is broken when the defect passes through one of the two coils.

Here, in the bridge type probe (as shown in FIGS. 1 and 2), using the principle that the balance of the voltages induced in the two coils 110 and 120 is broken is implemented by constructing a bridge circuit, in which a test coil is positioned at one side and impedance balance is placed at the other side so as to defect a change in the balance between the two sides by mean of a galvanometer.

As described above, according to the sensor for detecting surface defects of a metal tube, it is possible to overcome the problem that the conventional coil, provided in a direction vertical to the axial direction, cannot detect a defect in the circumferential direction, by inserting a plurality of coils having a predetermined inclined angle into the inside or the outside of the metal tube.

Moreover, the present invention has an advantage in that it is possible to detect the position of a defect generated in any direction by applying an alternating current to the coils so that the flow direction of the eddy current generated in the conductor such as the metal tube has a symmetrical or different inclined angle.

As above, preferred embodiments of the present invention have been described and illustrated, however, the present invention is not limited thereto, rather, it should be understood that various modifications and variations of the present invention can be made thereto by those skilled in the art without departing from the spirit and the technical scope of the present invention as defined by the appended claims.

What is claimed is:

1. A sensor for detecting surface defects of a metal tube, the sensor comprising a plurality of coils wound at a predetermined inclined angle, wherein the plurality of coils is inserted into the inside of a metal tube and an alternating current is applied to the coils to measure a change in impedance of the coils due to a change in an eddy current generated in the metal tube, thus detecting a surface defect of the metal tube, wherein the plurality of coils performs the roles of an exciting coil for generating an eddy current and a sensing coil for detecting the change in the impedance of the coils at the same time so as to detect a defect using a principle that a balance of a voltage induced in one coil and a voltage induced in the other coil is broken when the defect passes through one of the coils.

2. The sensor for detecting surface defects of a metal tube of claim 1, wherein the plurality of coils are divided into an exciting coil for generating an eddy current and a sensing coil provided on the outside of the exciting coil and detecting the change in the impedance of the coils, the sensing coil detecting a change in the eddy current generated in the metal tube by applying an alternating current to the exciting coil.

3. The sensor for detecting surface defects of a metal tube of claim 1, wherein each of the plurality of coils has a different inclined angle.

4. The sensor for detecting surface defects of a metal tube of claim 1, wherein the plurality of coils has a different inclined angle and wound symmetrical with respect to a virtual line vertical to an axial direction.

5. The sensor for detecting surface defects of a metal tube of claim 1, wherein the plurality of coils has the same inclined angle and wound parallel to each other.

6. A sensor for detecting surface defects of a metal tube, the sensor comprising a plurality of coils wound at a predetermined inclined angle, wherein the plurality of coils is inserted into the outside of a metal tube and an alternating current is applied to the coils to measure a change in impedance of the coils due to a change in an eddy current generated in the metal tube, thus detecting a surface defect of the metal tube, wherein the plurality of coils performs the roles of an exciting coil for generating an eddy current and a sensing coil for detecting the change in the impedance of the coils at the same time so as to detect a defect using a principle that a balance of a voltage induced in one coil and a voltage induced in the other coil is broken when the defect passes through one of the coils.

7. The sensor for detecting surface defects of a metal tube of claim 6, wherein the plurality of coils are divided into an exciting coil for generating an eddy current and a sensing coil provided on the outside of the exciting coil and detecting the change in the impedance of the coils, the sensing coil detecting a change in the eddy current generated in the metal tube by applying an alternating current to the exciting coil.

8. The sensor for detecting surface defects of a metal tube of claim 6, wherein each of the plurality of coils has a different inclined angle.

9. The sensor for detecting surface defects of a metal tube of claim 6, wherein the plurality of coils has a different inclined angle and wound symmetrical with respect to a virtual line vertical to an axial direction.

10. The sensor for detecting surface defects of a metal tube of claim 6, wherein the plurality of coils has the same inclined angle and wound parallel to each other.

* * * * *